US007311660B2

(12) United States Patent
Gomez

(10) Patent No.: US 7,311,660 B2
(45) Date of Patent: Dec. 25, 2007

(54) METHOD AND APPARATUS FOR HEATING AND APPLYING WARM ANTIFOG SOLUTION TO ENDOSCOPES AS WELL AS A DISTAL LENS PROTECTOR

(76) Inventor: Ricardo Alexander Gomez, 571 Main St., Amherst, MA (US) 01002

( * ) Notice: Subject to any disclaimer, the term of this patent is extended or adjusted under 35 U.S.C. 154(b) by 238 days.

(21) Appl. No.: 10/826,866

(22) Filed: Apr. 16, 2004

(65) Prior Publication Data

US 2005/0234301 A1    Oct. 20, 2005

(51) Int. Cl.
*A61B 1/06* (2006.01)

(52) U.S. Cl. .................. 600/169; 600/101; 600/133; 126/263.04; 126/263.06; 126/263.08; 126/263.09

(58) Field of Classification Search ............ 600/101, 600/133, 175–177, 153, 156, 157, 102; 607/112, 607/114; 126/263.02, 263.07
See application file for complete search history.

(56) References Cited

U.S. PATENT DOCUMENTS

| | | |
|---|---|---|
| 5,172,683 A | 12/1992 | West |
| 5,351,675 A | 10/1994 | Brodsky |
| 5,382,297 A | 1/1995 | Valentine et al. |
| 5,549,543 A | 8/1996 | Kim |
| 5,647,840 A | 7/1997 | D'Amelio et al. |
| 5,651,757 A | 7/1997 | Meckstroth |
| 5,910,106 A | 6/1999 | Morgan et al. |
| 6,231,596 B1 | 5/2001 | Collins |
| 6,234,635 B1 | 5/2001 | Seitzinger et al. |
| 2002/0022762 A1 | 2/2002 | Beane et al. |

*Primary Examiner*—Linda C. M. Dvorak
*Assistant Examiner*—Matthew J. Kasztejna

(74) *Attorney, Agent, or Firm*—McCormick, Paulding & Huber LLP

(57) ABSTRACT

A sterile, self-contained, disposable apparatus used for heating and applying solution to the distal end of endoscopes as well as an endoscopic lens protector. The heating mechanism is chemical, electrical or a combination of both. Further the apparatus serves as a self sealing container for the storage and application of anti-fog solution. By placing the apparatus over the distal scope prior to surgery, the scope is protected from damage from other instruments or trays. At the same time the distal lens is submerged in the warm anti-fog solution and it is uniformly and completely coated. Heat is transferred to the instrument from the solution in one example to act as an important and additional measure to prevent fogging of the lens. By heating the solution and the instrument, the drastic temperature difference between the interior of the body (98.6) and the instrument is eliminated. This inhibits the condensation of moisture, which always occurs upon inserting the cool scope inside the warm body. The apparatus combines the use of an anti-fog solution as well, which helps prevent fogging during the procedure when smoke and heat is generated within the body during the procedure. Lastly, the apparatus is designed to be used as a holder of the scope while protecting it from impact with a shock absorbent outer shell prior to, during, and after the medical procedure. A new method for defogging endoscopes by which a sterile protective device is combined with a defogging mechanism and placed over the distal lens of endoscopes prior to the medical procedure, used intermittently during the procedure, then placed over the lens at the end of the procedure. The apparatus is not removed until scope reaches the cleaning facility. This apparatus is ideal for sterile operations where the instrument is used intermittently and repeatedly.

17 Claims, 12 Drawing Sheets

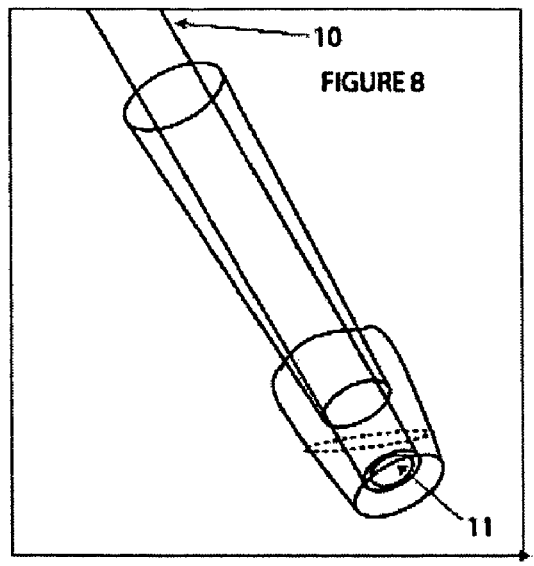
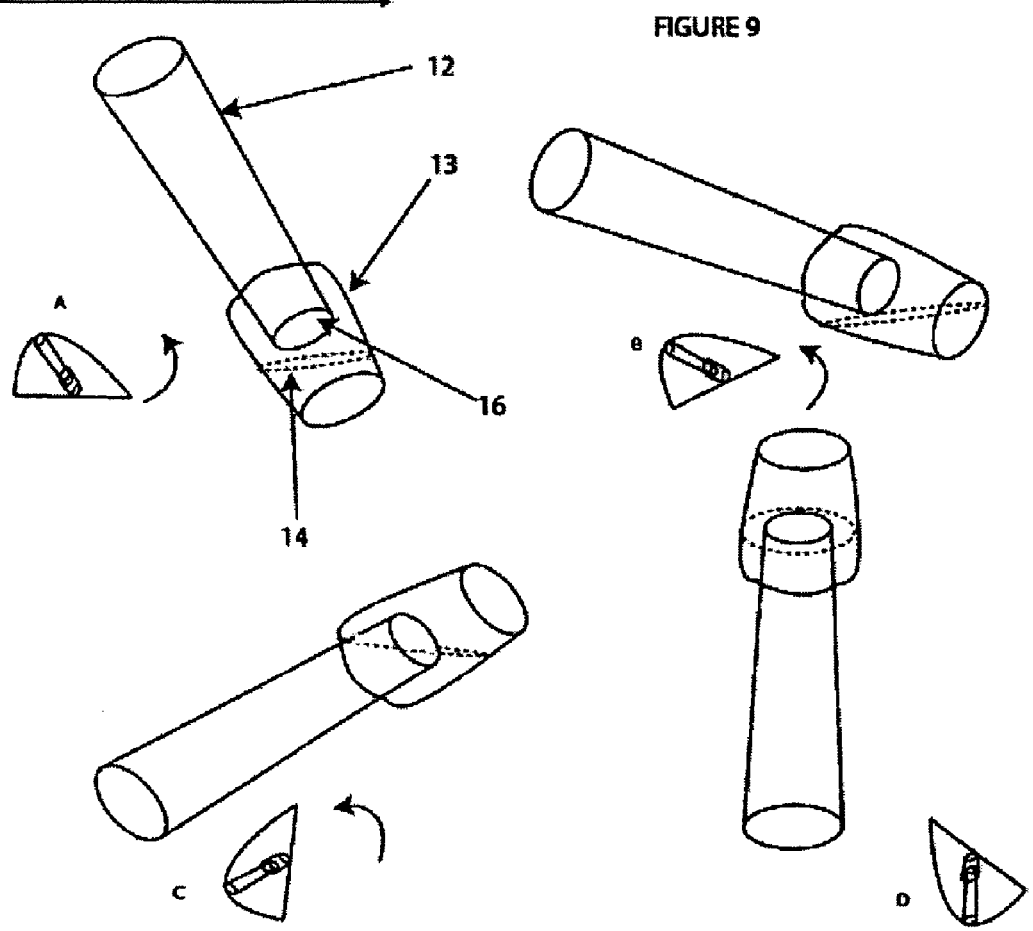

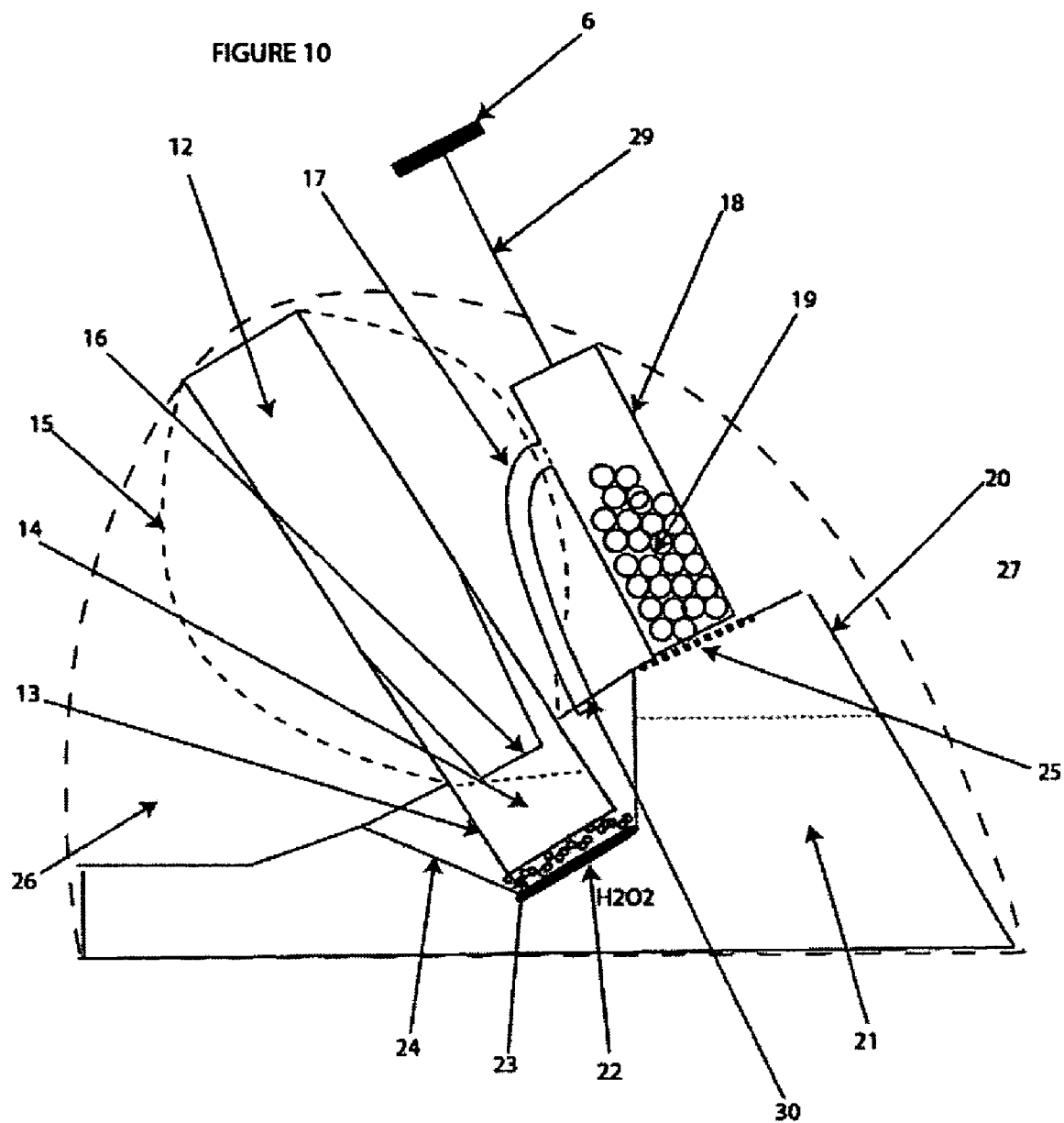

METHOD AND APPARATUS FOR HEATING AND APPLYING WARM ANTIFOG SOLUTION TO ENDOSCOPES AS WELL AS A DISTAL LENS PROTECTOR

FIELD OF INVENTION

The present invention relates to endoscopy and laparoscopy aezscopes used in minimally invasive surgery and other medical procedures. More particularly, the present invention relates to a sterile, compact, disposable apparatus used for heating, applying anti-fog solution, and protecting of the surgical scope lens prior to and during a surgical procedure.

BACKGROUND

Over the last two decades the use of endoscopic and laparoscopic optical scopes to perform surgery has grown exponentially. Today, in the United States more than 98% of the 770,000 gall bladder surgeries are performed using the help of an optical scope. Laparoscopes allow the surgeon to view the interior of the body cavity through a very small opening. By having this view, surgeons can then insert thin long instruments through other small incisions an remove virtually any internal organ. Many procedures once done through a large opening in the abdomen can now be done with the small incisions. The benefits of endoscopic surgery are tremendous. From the birth of endoscopic surgery to the very present surgeons have continually dealt with a persistent and annoying problem, the fogging of the scope lens. The fogging of the scope is not only inconvenient but is actually very costly. When scopes fog up during surgery, the surgeon cannot see and must pause the surgery until the picture clears up. This routine commonly occurs at least several times every procedure. With the incredible costs relating to anesthesia and surgical staff, every extra minute wasted truly equals hundreds and thousands of dollars. At the present time, anti-fogging solution is the method most commonly used to try and solve the fogging problem. Although they work well during the case, defogging solutions fall short in several ways. The main reason defogging solutions do not work is because they are applied improperly. Normally defogging solution is placed on a pad. The surgeon dabs the pad and wipes off the lens. In order for anti-fogging solutions to work effectively, they must be allowed to rest on the lens for some time and not be quickly wiped off. Another major downfall of anti-fog solutions relates to temperature. The temperature in the Operating Room is kept at abnormally cold level to inhibit bacterial growth. This environment cools the scope and the defogging solution prior to surgery. When the scope is inserted into the body, the moist hot environment in the body causes water to condense on the lens. The surgeon must wait until the scope equalizes temperature before beginning the case. Another problem is that during the procedure the surgeon usually has to reapply the defogging solution. Every time this is done the cold solution cools the lens and repeatedly causes the same initial condensation until temperature equilibrium is reached. Cumulatively, this wastes precious operating time. Another problem with current defogging solution methods is that they are messy, very wasteful, and potentially dangerous. Defogging solutions come within a small bottle with a small pad. The small pad is brought up to the operative site and the solution is poured on the pad. The solution is often spilled or drips away from the pad soaking the drapes on the patient. Also, the applicator pads are not usually radiolucent. If there is an emergency and the surgeon is forced to make a large incision, the pad could unintentionally be introduced into the body and would be undetectable by X-Ray. Another technique to prevent fogging is to try and heat the scope prior to inserting it into the body. One common method used to heat the scope for surgery is to place the scope in a bucket of warm saline or wrap the scope in a warm moist towel before the case begins. These methods are highly inefficient. The cold temperature in the room quickly cools down the warm towels and the warm saline. Using extra supplies such as sterile buckets, saline, and towels wastes money. Scopes are very expensive, so it is very dangerous to place the scope standing upright in a bucket; it can unintentionally be knocked over and damaged. Also, the bottom of the bucket or the towels easily scratches the lens. Scratched or damaged lenses is a major problem for hospitals. The estimated yearly cost to hospitals for endoscope repair is in the millions of dollars. Protecting scopes from damage is very important. Unfortunately, none of the apparatuses designed to heat endoscopes prior to surgery have attained commercial success for several reasons. Primarily, they are all either not practical due to high cost, time intensive set up or do not address the need to control fogging during the procedure and are only useful in preventing fogging at the beginning of the case. Another major downfall is that they try to replace anti-fog solution with only heat as oppose to combining the benefits of each other. It is well known that heating the optical scope prior to insertion into the body prevents fogging. It is also clear from the clinical experience that defogging solutions work well to prevent fogging during the case. What is needed is an apparatus that combines the benefits of both heat and anti-fog solution in order to provide superior defogging protection during the entire procedure.

SUMMARY OF THE INVENTION

The present invention presents an apparatus that combines the benefits of both heat and anti-fog solution therefore providing superior anti-fogging protection during the entire procedure. The apparatus is a self-contained disposable sterile apparatus for heating and applying warm anti-fog solution. The apparatus is compact and designed to be placed over the distal lens of endoscopes prior to medical procedure. By allowing the scope lens to bathe in the warm defogging solution prior to the procedure, as opposed to just wiping it the solution on and off, the effectiveness of the defogging solution is greatly increased. The apparatus includes a solid foam outer shell with an interior divided into several compartments. A reservoir in the center of the apparatus is filled with anti-fog solution. Surrounding the reservoir are the compartments have reactants within them. When a seal is purposely broken and the chemicals are intermixed a series of exothermic reactions occurs. The heat generated from the reaction is used to heat the center solution receptacle. The instrument is inserted into the self sealing hollow to be submerged within the solution residing in the receptacle. The instrument is simultaneously heated and bathed in the warm solution. The hard frame and soft interior create a barrier around the delicate instrument. This protects the expensive scope from damage potentially caused by other instruments and trays prior to and when not in use during surgery. Protecting the scope is a very beneficial attribute since scopes are very expensive and are frequently scratched or damaged during cases costing hospitals a great deal of money. By heating the solution and the instrument, the drastic temperature difference between the interior of the body (98.6) and the instrument is eliminated.

This inhibits the condensation of moisture, which always occurs upon inserting the cool scope inside the warm body. By also combining the use of a defogging solution, fogging is further prevented during the procedure when smoke and heat is generated within the body during the procedure.

BRIEF DESCRIPTION OF THE SEVERAL VIEWS OF THE DRAWING

These objects and features of the invention will be more clearly understood from the following detailed description along with the accompanying drawing figures, wherein:

FIG. 8. View of scope inside sheath with lens submerged in solution within reservoir FIG. 9. Mechanism for preventing the solution inside reservoir from spilling out when apparatus is turned upside down.

FIG. 10. Enlarged transparent side view of apparatus showing internal components necessary for the fast starting sustained exothermic reaction.

FIG. 11. Arrows showing downward pressure is applied to the external extension of the Cylinder containing Iron oxide catalyst.

FIG. 12. Catalyst containing cylinder pushes through seal and enters Hydrogen Peroxide (H2O2) filled lower chamber. Iron oxide pellets fall out of cylinder and enter H2O2 solution. Iron pellets are attracted and move towards magnet below cup shaped indentation.

FIG. 13. Iron oxide pellets congregate around magnet. Decomposition of H2O2 begins to occur. Oxygen gas generated from the decomposition reaction begin to rise to the upper part of lower chamber.

FIG. 14. Oxygen gas continues to be generated by the decomposition of H2O2. Oxygen gas continues to accumulate in upper part of lower H2O2 filled chamber. Pressure begins to raise pushing H2O2 inside the empty cylinder.

FIG. 15. Oxygen gas continues to be slowly generated in lower chamber. The Oxygen pressure continues to rise and the H2O2 inside the hollow cylinder is forced through the tube into the space surrounding the reservoir which contains powdered Iron Oxide catalyst.

FIG. 16. H2O2 continues to enter space-surrounding reservoir. The small amount of H2O2 that enters the space is overwhelmed by the powdered catalyst and Instantaneously Decomposes into water and Oxygen releasing great deal of heat upon contact with powdered iron catalyst. Heat is quickly transferred to reservoir and solution within the reservoir. Oxygen generated from the fast decomposition reaction occurring in the space around reservoir, rises into the upper chamber and begins to slowly exothermically oxidize the unoxidized iron material heating the surrounding sheath and upper part of reservoir FIG. 17. Oxygen gas pushes the remainder of H2O2 out of tube. O2 gas continues to be slowly generated in lower chamber. Oxygen gas passes through hollow cylinder, through tube into space surrounding reservoir. Once inside the space the Oxygen gas quickly rises and begins to fill the upper chamber. The Oxygen gas slowly and for a sustained period of time exothermically oxidizes the unoxidized Iron material heating the sheath and upper part of reservoir. The slow Decomposition of Hydrogen Peroxide in the lower chamber maintains a constant supply of oxygen generation and also maintains the space around the reservoir heated.

DETAILED DESCRIPTION OF THE INVENTION

Figure 1A:
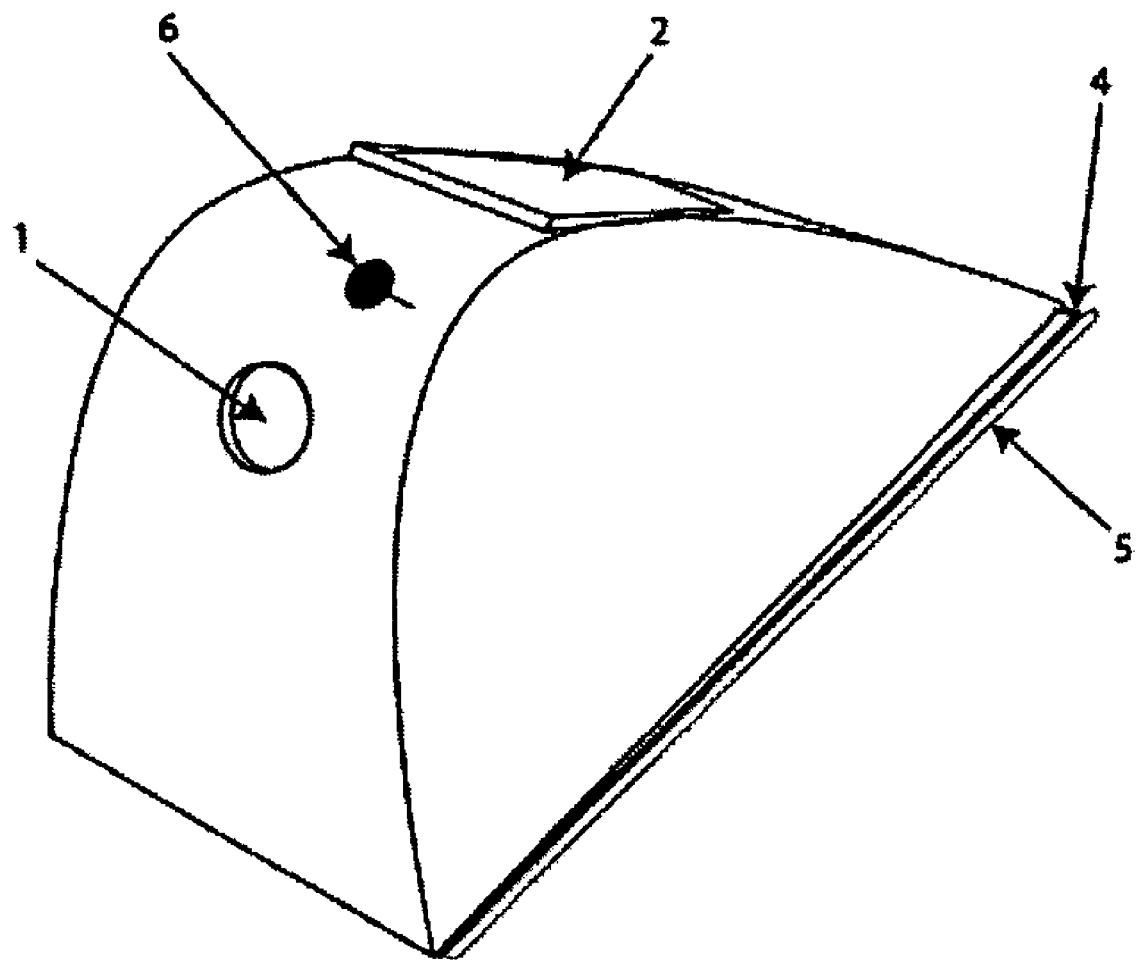
FIG. 1a. Three-dimensional front/side view of apparatus with vents
Figure 1B:
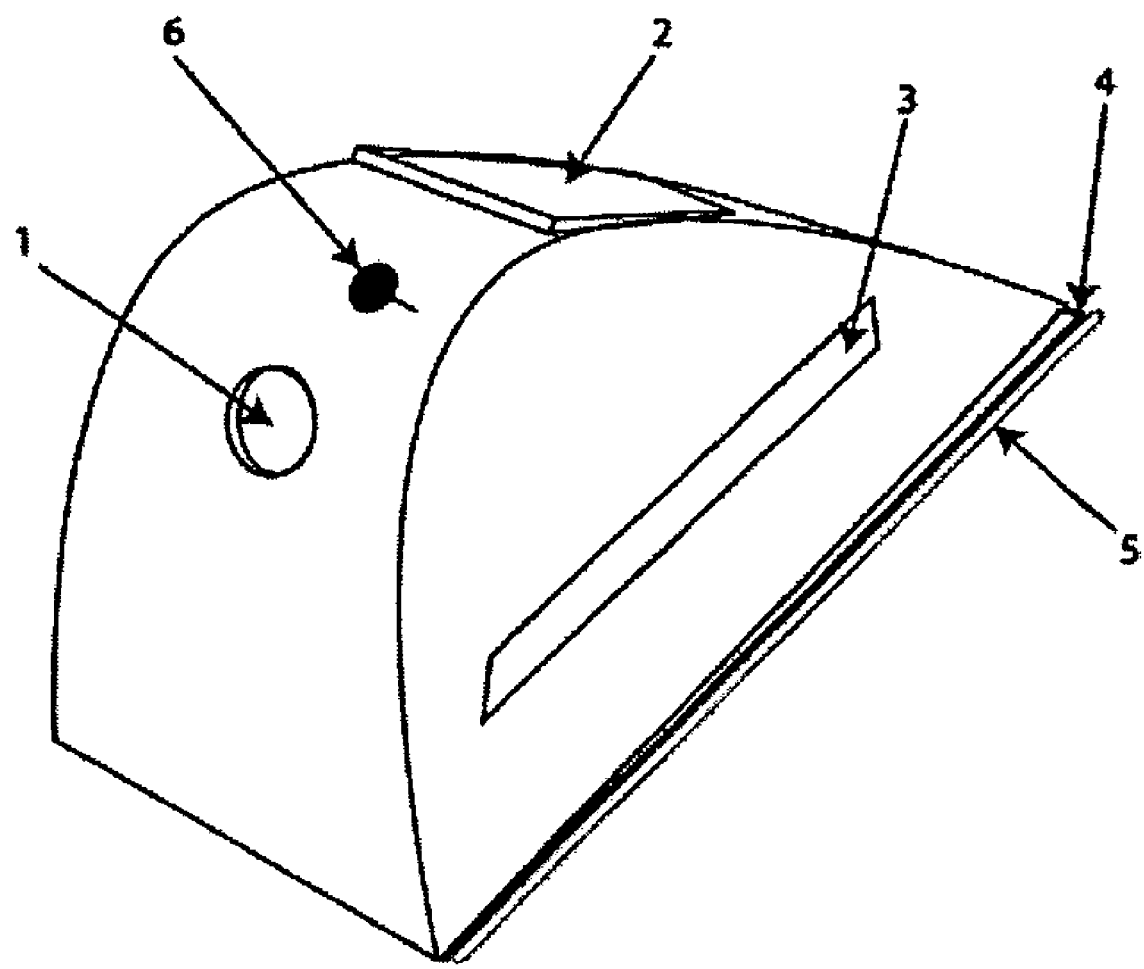
FIG. 1b. Three-dimensional front/side view of apparatus without vents
Figure 19:
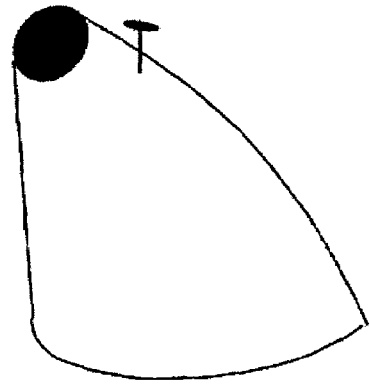
FIG. 19. Alternative tubular outer shape of apparatus

In one particular embodiment the apparatus described in this invention comprises of an outer shell (27) made of a foam material or any solid yet shock absorbing insulating material. This shell is designed to protect the lens of the scope or any other type of instrument from damage prior, during, and after the procedure. The material has to also be inexpensive since the apparatus is disposable and for single patient use. The outer shell cover is preferably constructed of any high density Polyurethane, Etha, Viscoelastic, Latex foams, or the like. It can also be made from rubber foam. A Semi-flexible thermoplastic can also be used. The outer shell can also be made from Insulating cardboard or a thick insulating fabric. The outer shell can alternatively be constructed out of a plastic frame covered by a silicone rubber or insulating plastic. It is important that the material have good shock absorbing and insulating properties The outer shell is preferably in the shape of a tear drop as in FIG. 1 but can alternatively be made in any shape; square or spherical, clearly shown in FIG. 19 and FIG. 20. The apparatus can also have a tubular shape. The apparatus can have rounded corners or square corner. The entire apparatus exteriorly is preferably 4 inches long, 3.5 inches wide, and 4 inches high but can be as small as 2 inches wide and 2 inches long and 2 inches high. Alternatively the apparatus can be as large as 6 inches wide, 6 inches long and 8 inches high. Clearly, the apparatus can be sized to conform the shape of any instrument used.

Figure 5:
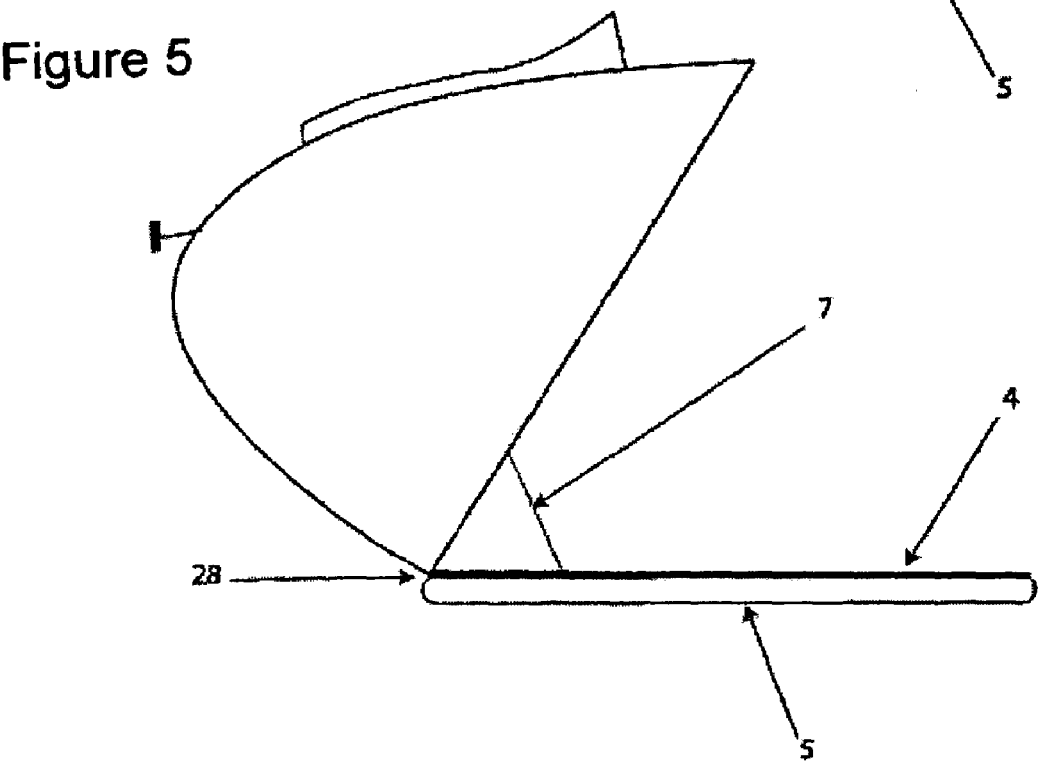
Figure 6:
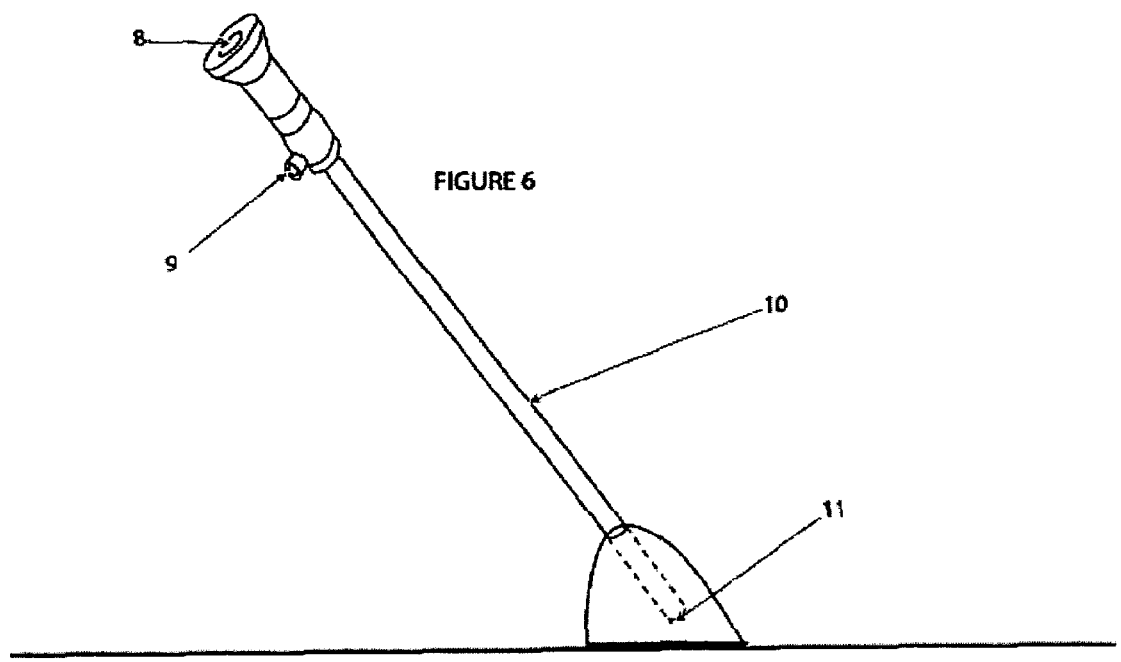
FIG. 6. Side view of scope inserted in to apparatus vertically showing size relationship.
Figure 7:
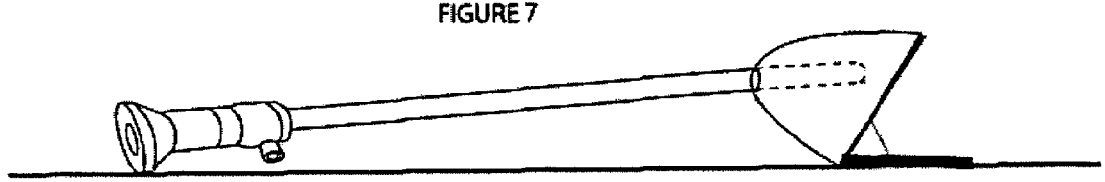
FIG. 7. Side view of scope inside apparatus lying flat with flap mechanism fully extended.

On the bottom of the outer shell contains solid flap (4), which can have the same perimeter as the base of the outer shell. This flap is attached only at the front bottom part of the apparatus creating a hinge (28). The flap is also attached in the middle by two elastic bands (7). The flap can be constructed of a high-density foam material, cardboard or plastic. The external face of the bottom flap has an adhesive material (5) that has a protective cover until it is needed. When the surgery begins and the surgeon brings the apparatus up to the operative field he can secure the apparatus anywhere on top of the drapes by removing the protective cover from adhesive bottom and sticking the apparatus anywhere on the operative field. The function of the flap is so that the scope can be inserted vertically (FIG. 6) but when it is not in use, is the flap mechanism allows the apparatus to rotate horizontally while the scope remains inside the apparatus as shown in FIG. 5 and FIG. 7. Although the apparatus rotates along the hinge (28), the flap maintains it securely attached to the drapes by the adhesive flap. Alternatively, the apparatus may be constructed without the flap and the adhesive can be placed directly on the bottom of the apparatus. Also the apparatus can be secured on any surface through such devices as but not limited to: adhesives, screws, magnetism, mounts, clips, or VELCRO.

The exterior of the apparatus may contain a soft, non-scratch, absorbent sponge in the uppermost part (2). The sponge can be square in shape or in the shape of a rectangle. Alternatively the sponge can be in the shape of an eclipse or a circle. The sponge can be ¼ to ¹⁄₁₆ of an inch thick. This sponge is used to wipe the excess defogging solution from the scope after it is removed from the apparatus and can also help with cleaning blood from the scope when it is removed from body cavity.

Figure 2:
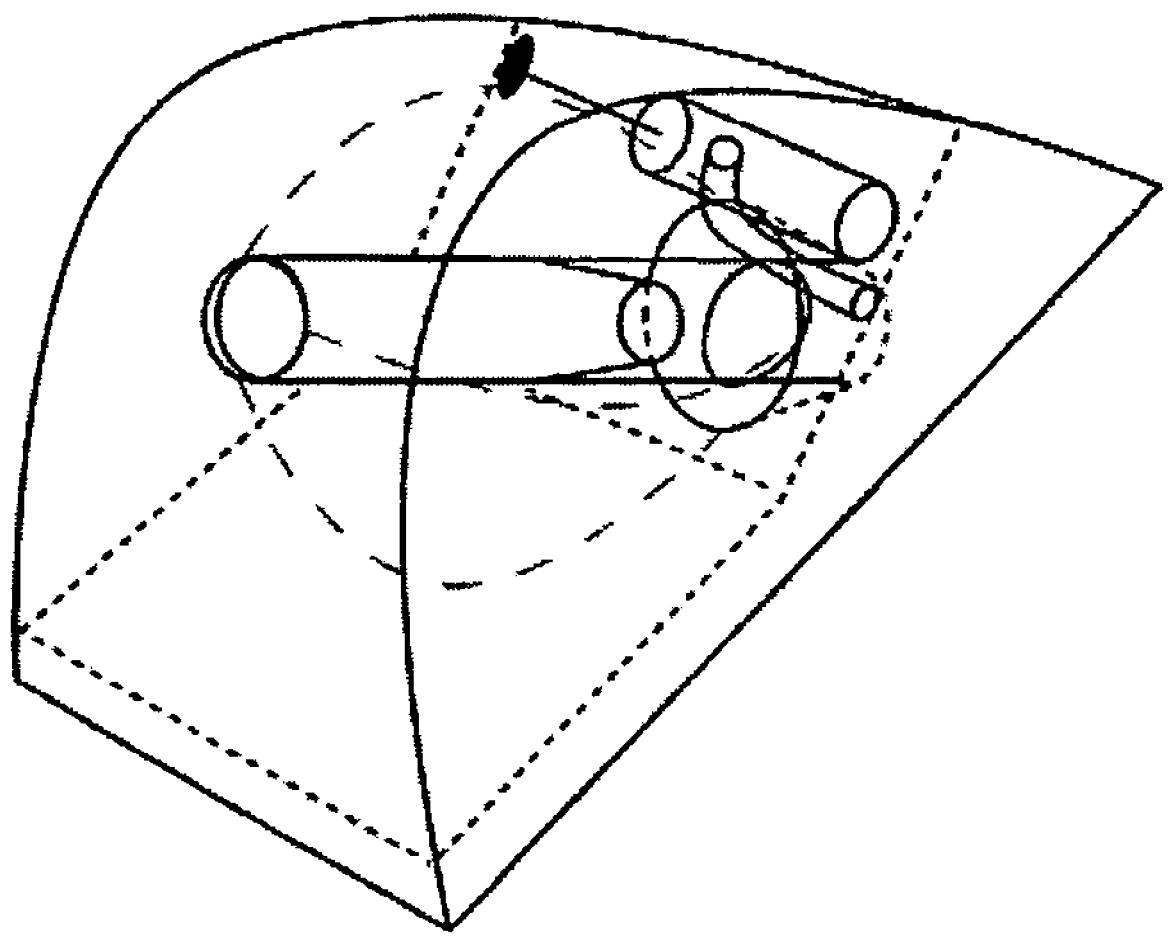
FIG. 2. Three-dimensional transparent front/side view of apparatus with internal contents FIG. 3. Three-dimensional transparent posterior/top view of apparatus with internal contents FIG. 4. Side view of apparatus FIG. 5. Side view of apparatus with bottom flap mechanism fully extended.
Figure 3:
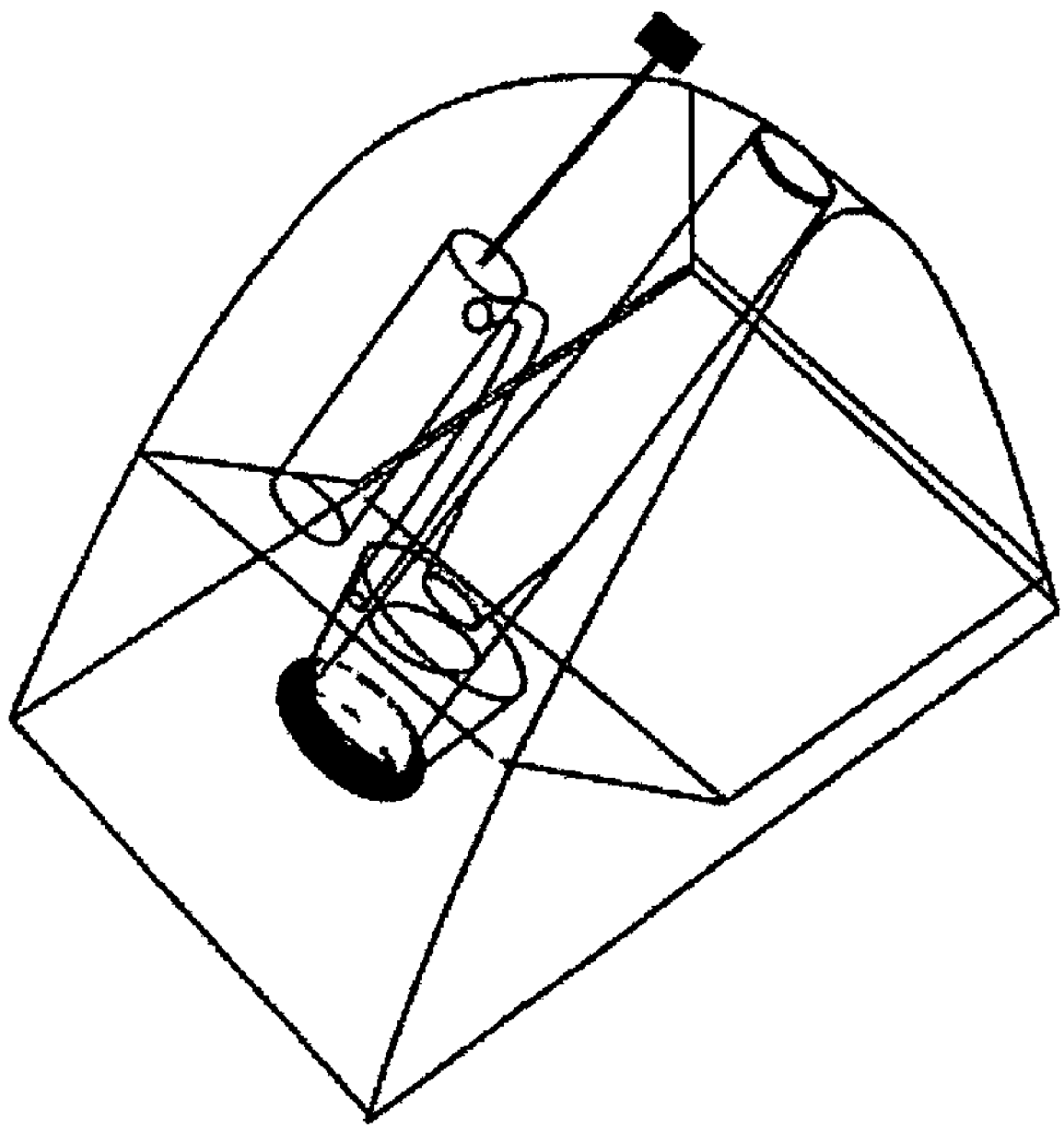
Figure 4:
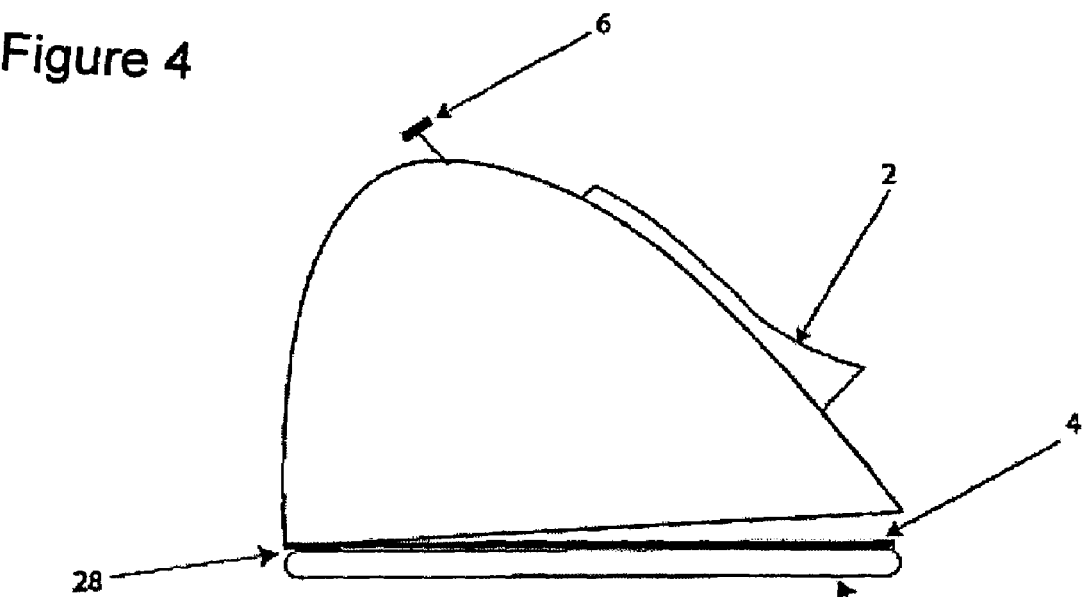

Internally the apparatus contains a center sheath (12). This center sheath has a center canal that accommodates the scope. This sheath preferably runs directly down the center or the apparatus from the upper front to the lower back as shown in FIG. 2. The sheath can alternatively run directly down the center or lateral to the center. The location of the sheath can be in any configuration as long as uniform thermal conductivity is achieved. The length of the sheath is preferably 3 inches long but can be as long as 8 inches. The sheath has the shape of a tube but can also be constructed of two flat pieces attached together in the upper and lower thirds leaving a tubular canal in the middle. The tubular space inside the sheath can be 5 mm or up to 10 mm, or any length depending on the instrument intended to be used. One embodiment of the sheath is preferably constructed of but not limited to a thin piece of high-density Polyurethane, Etha, Viscoelastic or Latex foams. It can also be made of rubber foam or thin plastic. A water impermeable fabric can also be use. The sheath can alternatively be constructed of silicone or rubber.

The most distal or innermost part of the center sheath (16) penetrates a reservoir (13). This reservoir can be constructed of the same material as the sheath but is preferably made from a metal or any good heat conducting metal such as iron, aluminum, steel, and copper. The reservoir itself can also be made of a magnetic metal material. The reservoir can be in the shape of a box or a cylinder (13). It can be anywhere from ½ an inch to 2 inches long and wide enough to accommodate at least a 5 mm to 10 mm scope and still allow some space around the scope. The reservoir is preferably filled with a defogging solution (14). The defogging solution can be made of a combination of water, glycol, and a water-soluble wetting agent but not limited to such. Alternatively, the defogging solution used can be any commercially available surgical defogging solution such as F.R.E.D ™. The reservoir can also be filled with only plain water or saline. Ideally any chemical able to enhance or facilitate the use of an instrument may be used.

Internally, inside the canal between the reservoir filled with defogging solution and the central sheath is a valve mechanism as shown in FIG. 9. The valve mechanism is preferably constructed by enclosing the reservoir around the distal aspect of the sheath while at least 1 inch overhangs. The valve mechanism preferably resembles a tube within a tube. FIG. 8 and FIG. 9 shows the tube within a tube mechanism that allows for the scope to enter the reservoir and make contact with the solution (FIG. 8) but prevents any fluid from spilling out of the reservoir when the apparatus is turned upside down (FIG. 9) with the scope removed. The way it liquid is prevented from falling out functions by creating a pocket around the distil end of the sheath. When the sheath is turned with the reservoir down all the liquid will fall into the reservoir. As the sheath and reservoir are turned upside down, the liquid slides along the side and enters the pocket surrounding the distal sheath. Alternatively, the valve mechanism can also resemble a heart valve or be made with a flap and a hinge that only opens in one direction. The valve can also resemble a valve in a human vein. The valve can be a ball and socket mechanism in which a ball inside the reservoir plugs the hole when the reservoir is turned upside down but still allows for the scope to enter in the other direction. The valve mechanism can be constructed from a plastic material. It can also be made from the same material used for the sheath such as a high-density foam or water impermeable fabric. The valve can also be made of metal, aluminum, or silicone. The valve can be any self sealing mechanism known to person skilled in the art to prevent leakage and splash black of fluid.

The entire center sheath including the distal reservoir segment is surrounded by compound, that is unoxidized but can become easily oxidized and release heat energy when it is oxidized (15). Oxidation reactions are always exothermic, meaning that they always release heat. Metal compounds share the common characteristic that when in their elemental form they are prone to donate electrons and are easily oxidized. The metal preferably used to surround the sheath would be Iron or Fe. The iron is preferably in powder form but can be in pellets or as shavings garnering a large reactive surface area. The Iron used is preferably a commercially available mixture, which uses a combination or Iron, vercumilite, activated charcoal, and water. This commercially available mixture from (mycoal) or (heatmax) can provide up to 6 hours of heat when the iron is oxidized by atmospheric oxygen. Other metals such as Mg, Aluminum, Nickel or Copper can also be used. Unoxidized Non-metals can also be used in gas, powder, or liquid form. The material is preferably in an oxygen permeable membrane wrapped around the sheath. The amount of material surrounding the sheath can as thin as ⅛ of an inch to as thick as to fill the entire upper chamber (26). The unoxidized material can also be in liquid form surrounding the sheath and reservoir. It can also be in a bag surrounding the sheath and reservoir. The bag can be made of plastic or impermeable rubber foam. Any combination of reactants known to persons skilled in the art can be utilized to create the exothermic reaction.

The one embodiment for heating the defogging solution inside the reservoir as well as the long lasting sustained heating of the apparatus uses three separate exothermic reactions The first reaction uses the energy generated from a fast exothermic decomposition of Hydrogen Peroxide to heat the reservoir very quickly. The second reaction is a slower but consistent decomposition of H2O2. The third reaction uses the oxygen molecules generated in the first and second reaction to slowly oxidize the iron material surrounding the upper part of the reservoir and the central sheath and heat the apparatus for a longer sustained period of time.

Hydrogen peroxide (H2O2) is an unstable molecule, which quickly and spontaneously decomposes to H2O (water) and O2 (oxygen gas). The balanced equation of the reaction is H2O2+H2O2=2H2O+O2. This decomposition reaction is very exothermic. Although H2O2 decomposes spontaneously the rate is much to slow at room temperature. A catalyst is a molecule that facilitates and speeds up the rate of a given reaction. When a catalyst is added to H2O2 the decomposition of H2O2 speeds up greatly causing the H2O2 solution to heat up a large quantities of Oxygen gas are released. By controlling the amount of catalyst one can control the amount of Oxygen gas generated and the amount of heat released to the solution. In the preferred mechanism the catalyst used is Iron oxide. Alternatively the catalyst can be any molecule that speeds up the decomposition of H2O2.

Alternatively catalysts such as manganese dioxide, manganese (IV) oxide, silver catalyst, and potassium permanganate can also be used. The natural enzyme, catalaze that is designed to decompose H2O2 in plants and yeast can also be used. The catalyst is preferably in powdered form or in pellets. It can also be in shavings, crystals, and salt or in liquid form. The Shape and type of catalyst determines the precise rate of H2O2 decomposition. The Powdered form of catalyst is much more reactive than the pellet form because of the larger surface area.

FIGS. 11-18 illustrate the exact mechanism for activation and function of the preferred heating method. This method accomplishes two things. Upon activation, a fast reaction occurs and the solution in the reservoir is almost immediately heated above body temperature, the heated solution is then maintained above body temperature along with the interior of the apparatus for up to 7 hours.

FIG. 10 illustrates in detail all the components for an embodiment of the exothermic reaction. The interior of the apparatus comprises two chambers. One upper chamber (26), which contains the unoxidized material (15), surrounds the sheath (12) and a lower H2O2 containing chamber (20) The H2O2 is contained in a thermo plastic container. The container can alternatively by made from aluminum, copper, iron or any material suitable commonly known to persons skilled in the art. The H2O2 can also be kept in high-density Polyurethane, Etha, Viscoelastic or Latex foam or rubber foam container or any non reactive materials. The H2O2 could also be maintained in a heat resistant plastic or silicone bag. The H2O2 is preferably maintained in the lower part of the apparatus. Alternatively the H2O2 can also be stored in the back or upper part of apparatus. The H2O2 can also be maintained in a container outside the apparatus.

The H2O2 is stored in one embodiment, in a plastic chamber that also contains a cup shaped indentation (24), vacuole at the top part of the container. The indentation creates a space, which surrounds the reservoir (13). Inside the space surrounding the reservoir there is a small amount of powdered iron oxide catalysts (23). This catalyst is found between the reservoir and the internal floor of the cup shaped indentation. The indentation is at least large and deep enough to fit the reservoir and the surrounding unoxidized material. The indented cup exterior is inside the bottom chamber and is surrounded by H2O2 since it penetrates any where from ½ inch to three inches inside the H2O2 container (24). The external bottom of the cup shaped indentation contains a magnet (22) The indentation in the H2O2 filled container can be any shape as to allow the reservoir bottom and sides to be in direct contact with the H2O2, only separated by the plastic or material that makes up the wall of the H2O2 filled chamber. The cup shaped indentation can alternatively be devoid of a magnet. Alternatively the H2O2 can be completely separate without any indentation, and the reservoir can just sit above the H2O2 receptacle. In this specific mechanism, the H2O2 filled container has a hole in the uppermost part of the chamber. This hole is sealed by a thin film (25). Sitting directly above the film-covered hole in the upper chamber, is a cylinder or hollow tubular container (18) with one open end directly making contact with the film seal covering the hole (25). Preferably the hollow cylinder is made from plastic. The seal can also be constructed of aluminum, metal, ceramic, or any other suitable material known to persons skilled in the art. The film sealing the hole in the H2O2 filled container can be constructed of a thin plastic or aluminum paper or a thin water impermeable paper or fabric. Alternatively a one-way valve that is normally closed but can be opened when the plunger cylinder pushes through can also be used to create the seal.

The tubular hollow container sitting directly above the film-covered hole is filled with the iron oxide catalyst (19). The iron oxide catalyst is preferably in shavings or small pellets (19) the amount and shape of the catalyst controls the rate in which the decomposition of H2O2 occurs thereby controlling the generation of heat and oxygen. The Film covered hole on the upper wall of the H2O2 container is at least as wide as to allow the catalyst filled cylinder to slide through. The uppermost part of the cylinder is closed ended and has a solid extension to the exterior of the apparatus (29). The extension can be a small plastic rod. Alternatively it can be a wooden, metal or aluminum rod. This extension has a flat part in the exterior of the apparatus (6). Alternatively, the cylinder can be made without a plunger extension and the cylinder itself can be long enough to penetrate to the exterior of the apparatus. Any method commonly known to persons skilled in the art can be utilized to initiate the exothermic reaction.

In the upper part of the catalyst filled cylinder is a small tube (17). This tube is open on both ends. One open end is inside the catalyst filled cylinder and the other open end is inside the cup shaped indented space surrounding the reservoir (30) The tube creates an open communication between the inside of the catalyst filled cylinder and the space (24) containing powdered catalyst (23)surrounding the reservoir (13). The tube is preferably constructed out of flexible plastic, or rubber. Silicone, PVC, copper or aluminum tubing can also be used but is not limited to such.

Figure 11:
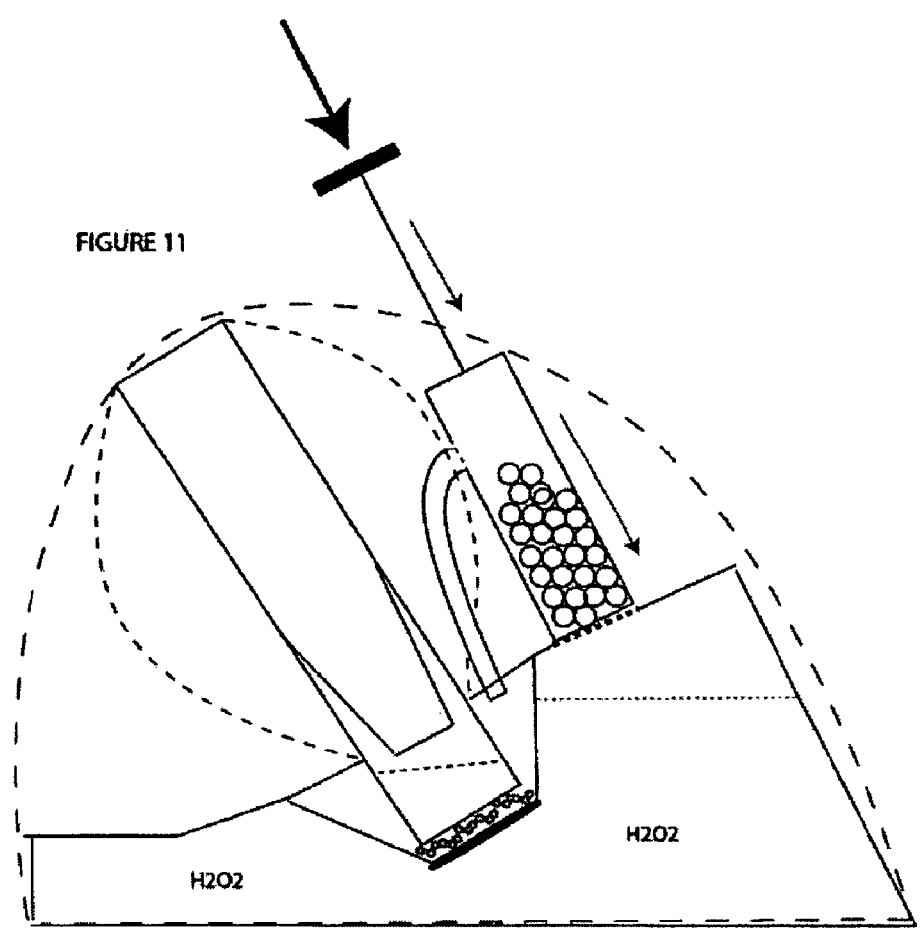
FIG. 11-17 Sequence of steps for the activation of the preferred exothermic reaction.
Figure 12:
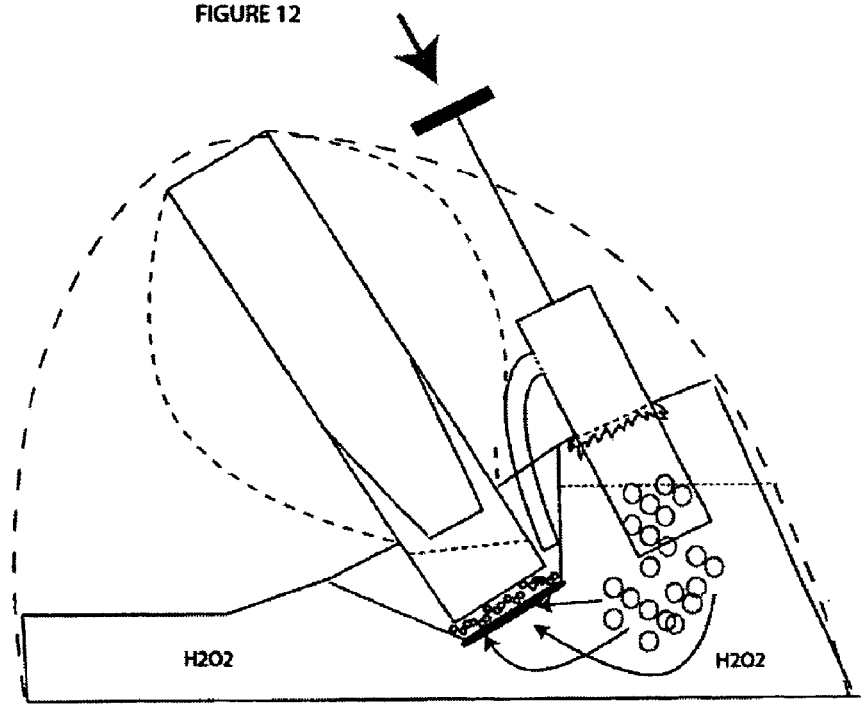
Figure 13:
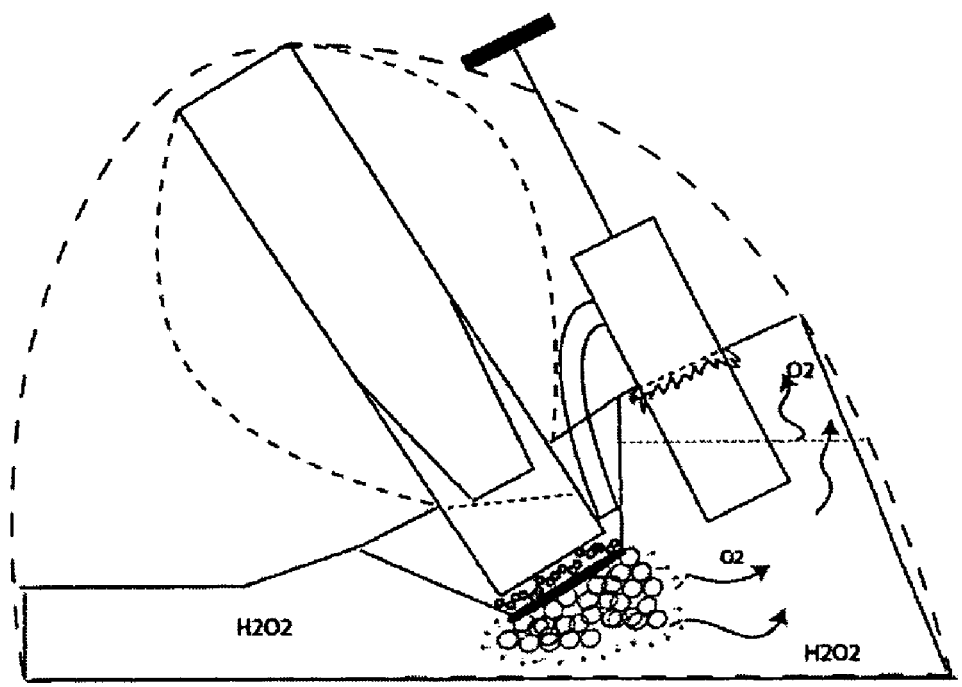
Figure 14:
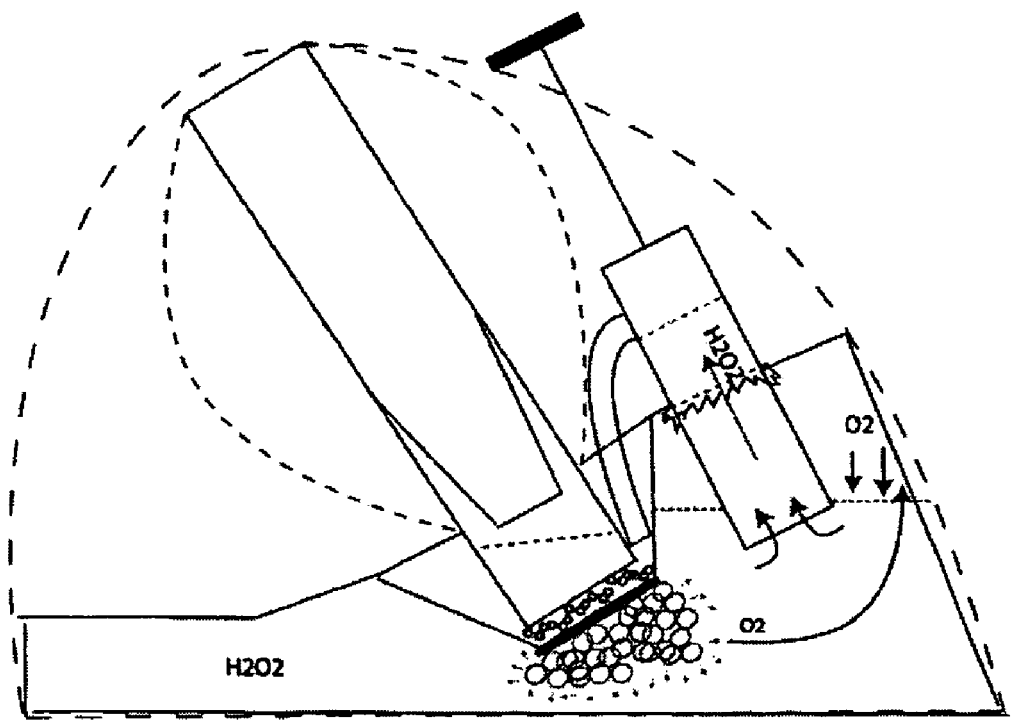
Figure 15:
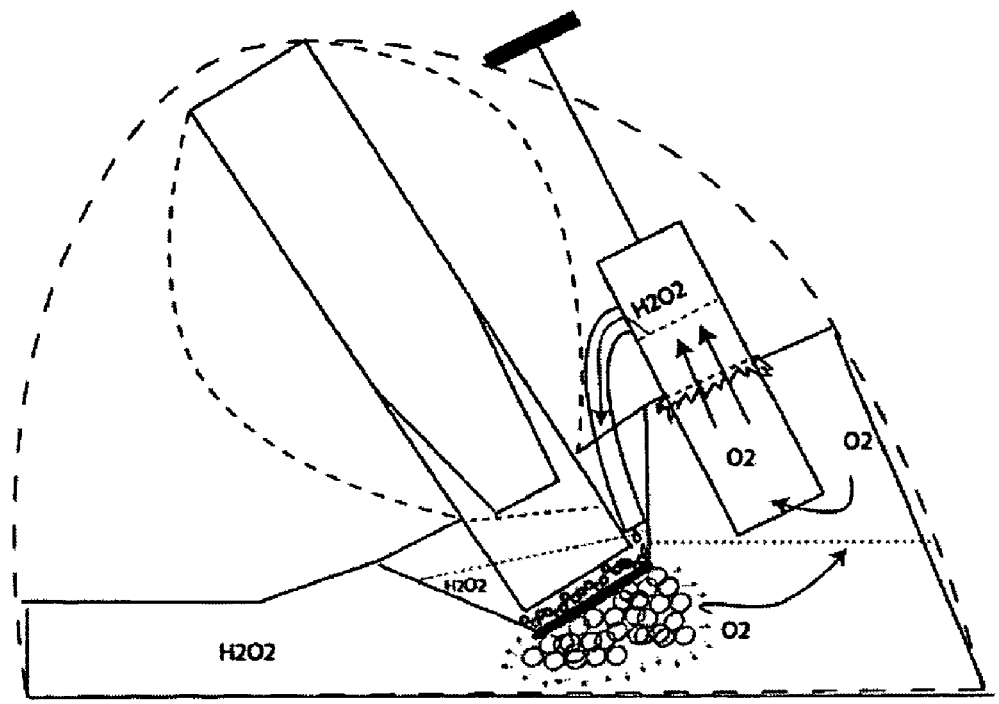
Figure 16:
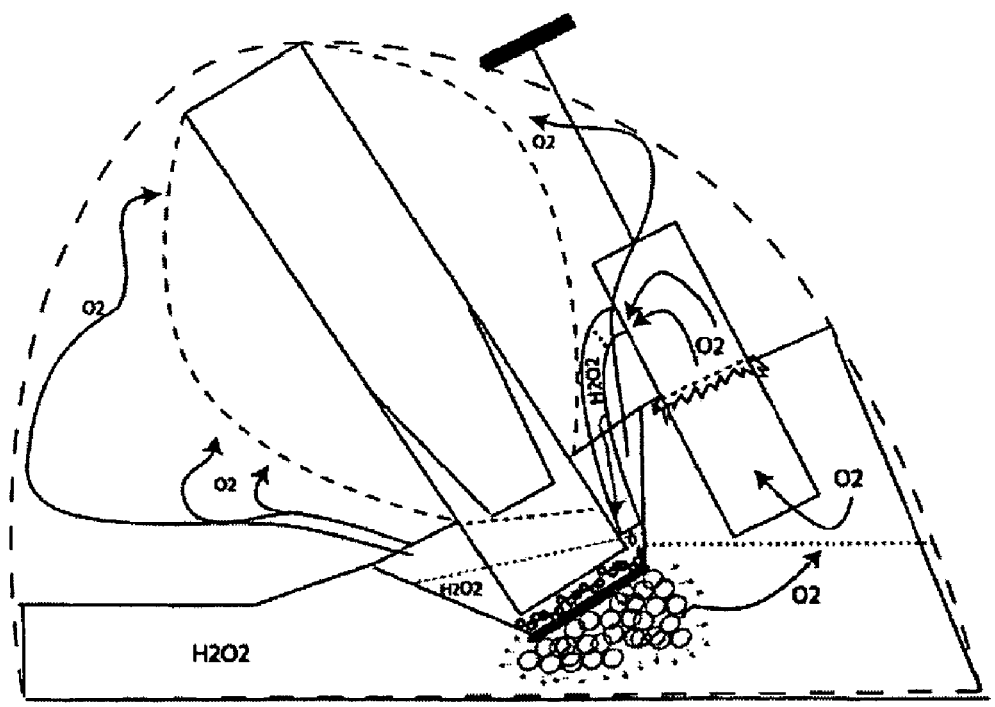

FIG. 11 illustrates the first step of one embodiment in the activation of the exothermic reaction. When activation is desired, downward pressure is applied to the external flat part (6) of the extension (29) of the catalyst-containing cylinder (18). Once the downward pressure is sufficient enough, the catalyst-containing cylinder (18) will break through the film or seal separating the lower chamber (25) the catalyst-containing cylinder will then enter the lower H2O2 containing chamber (FIG. 12). The cylinder is pushed about an inch deep into the H2O2 solution. Once the cylinder breaks the seal gravity will cause the Iron oxide pellets to fall out of the cylinder and enter the H2O2 solution. The H2O2 solution then begins to slowly decompose at a controlled speed that is dependant on the quantity and shape of the catalyst. As soon as the iron oxide catalyst fall out of the cylinder and enter the H2O2 solution the iron oxide pellets are attracted to the magnet (22) located in the external bottom of the cup shaped indentation. This causes all of the catalyst (19) to congregate around the magnet (FIG. 13). By having all of the catalyst congregate around the magnet, the H2O2 decomposition will only occur around the external aspect of the cup shaped indentation. The heat generated from the decomposition is therefore much more efficiently transferred to the space around the reservoir allowing for faster heating of the defogging solution in the reservoir. Alternatively the catalyst can also be introduced by having a double close ended, thin walled glass tube filled with the catalyst. When desired, the glass tube is broken and the catalyst is consequently introduced to the H2O2. Another method is to use a liquid catalyst and maintain it in a container or bag above or adjacent to the H2O2. When desired, a seal dividing the liquid catalyst and the H2O2 can be broken and the liquid catalyst is allowed drip into the H2O2. The rate of the decomposition and the amount of O2 generated can then be controlled by the rate and amount of the catalyst drip. Once the catalyst is introduced to the H2O2 chamber, the H2O2 begins to decompose at any predetermined rate.

Figure 17:
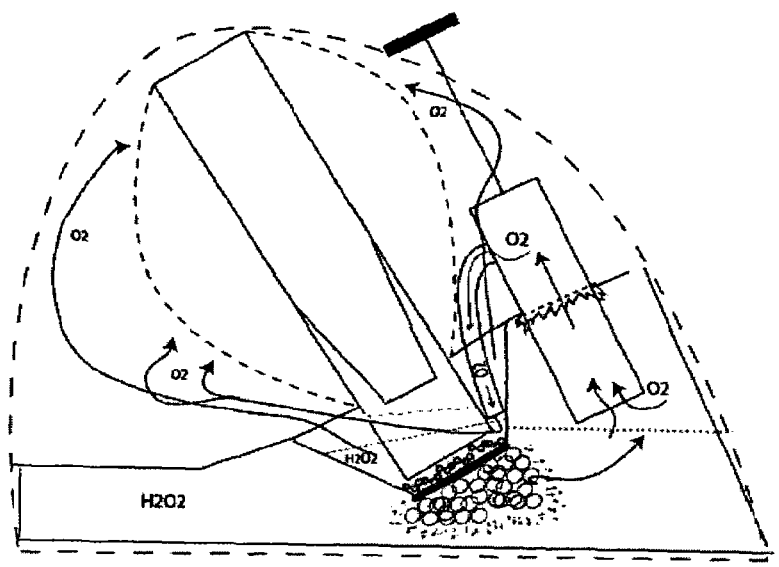
Figure 18:
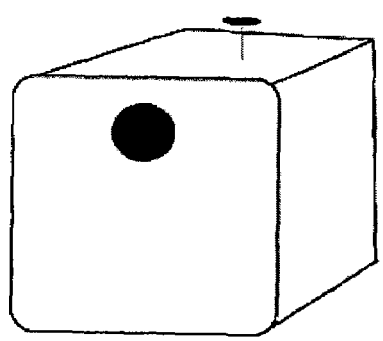
FIG. 18. Alternative square outer shape of apparatus

As shown in FIG. 13 the H2O2 begins to decompose into H2O and O2 gas the gas rises up to the top of the H2O2 containing chamber. (FIG. 14) shows the O2 gas building up in the top part of the H2O2 containing chamber. As more and more O2 is generated the pressure begins to rise. The pressure of the O2 gas pushes on the liquid and the H2O2 surrounding the cylinder begins to be pushed inside the cylinder. (FIG. 15) As the O2 pressure continues to raise even more the H2O2 that entered the cylinder is pushed in further. The H2O2 enters the small tube (17) and then flows out of the distal end of the tube (30) and into the interior of the indented cup shaped space (24). Since the H2O2 that enters the space around the reservoir is a small amount and the powdered iron oxide catalyst (23) has a large surface area, the H2O2 decomposes vigorously when it makes contact with the powdered iron catalyst. Large amounts of heat are quickly released and transferred to the reservoir. Since this reaction occurs in direct contact with the reservoir containing defogging solution (13) the solution inside the reservoir is virtually instantaneously heated. At the same time a bolus of Oxygen gas is generated inside the space from the fast decomposition reaction. This Oxygen gas quickly rises into the upper chamber and begins to exothermically oxidize the Iron Material (15) thereby heating the sheath and upper part of the reservoir. (FIG. 16) The O2 gas continues to be generated in the lower chamber increasing the pressure even more. The Oxygen gas travels into the empty cylinder (18) and then into the tube (17) pushing out all the remaining H2O2 into the space around the reservoir. After the ejection of the H2O2 into the indented space, the level of the H2O2 in the lower chamber becomes lower than the opening of the cylinder, H2O2 cannot enter the cylinder anymore and only the O2 gas generated passes into the cylinder. FIG. 17, once all of the H2O2 has completely entered the indented cup shaped space (24) The O2 gas that is slowly generated in the lower compartment flows through the hollow cylinder and into the tube then out to the indented space where it quickly rises into the upper chamber. As the oxygen begins to fill the middle chamber, the unoxidized iron material begins to get oxidized by the O2 gas. This exothermic reaction is much slower than the decomposition reaction since the O2 is introduced slowly, and thus the heating can be sustained for a long period of time. As the material exothermically oxidizes, heat is generated and transferred to both the sheath and reservoir, maintaining a sustained elevated temperature inside the apparatus. The interior of the apparatus and the solution inside the reservoir are maintained heated by both the heat generated by the H2O2 decomposition occurring in the lower chamber directly below the reservoir and also by the slow exothermic oxidation of the iron material in the upper chamber. The exothermic reaction can be sustained as long as desired by manipulating several factors. The quantity and concentration of the Hydrogen Peroxide, the rate of oxygen generation, which is determined by the speed of the decomposition reaction, and by the amount of, unoxidized iron material in the upper chamber. By generating the oxygen the apparatus can be self-contained and sealed completely from the environment as oppose to depending on atmospheric oxygen as the oxidizing agent. Also, by generating the oxidizing agent, one is able to control the amount and rate at which the oxygen is delivered, thus giving one control over the length of the exothermic reaction, speed of initiation, and the maximum temperature of the exothermic reaction.

The Oxygen molecule is preferably generated by the decomposition of 6% Hydrogen Peroxide but other concentrations below 30% will work. Alternatively, Oxygen can be generated from the decomposition of Potassium chlorate (KclO3). Also the oxygen can be generated from decomposition of oxides such as nitric oxide or Manganese dioxide. Oxygen molecules can also be generated by decomposition of salts such as Potassium nitrate. Oxygen can also be generated by the chemical decomposition of water or the electrolysis of water. The oxygen molecules can also come from atmospheric oxygen found in air.

The oxygen can be generated from the combination of two or more of the above methods. For example, some part of the oxygen can come from the decomposition of one of the mentioned chemicals and another part of the oxygen may come from atmospheric oxygen by way of a vent or opening in the exterior of the apparatus (13).

The heating of the apparatus and reservoir can alternatively be heated by using only atmospheric oxygen. The apparatus may contain small vents in the exterior (13). These vents can be covered by a seal. When the seal is removed the interior is exposed to atmospheric oxygen, therefore oxidizing the material around the sheath and reservoir heating the apparatus and the defogging solution in the reservoir In an alternative embodiment for the activation of the exothermic reaction, the H2O2 is stored in a syringe that has a tube connected to the space around the reservoir. The plunger is pushed from the exterior. The plunger pushes into the syringe thereby pushing the H2O2 out through the tube and into the bag surrounding the reservoir. Inside the bag is a catalyst (Iron oxide). Immediately upon mixing of the H2O2 with the catalyst the H2O2 begins to rapidly decompose. The heat generated from the reaction quickly heats the reservoir and solution inside reservoir. The plunger is fully inserted and all of the H2O2 is completely introduced to the bag surrounding the reservoir. As the H2O2 decomposes it releases Oxygen gas. The gas escapes through the upper part of the bag and immediately reacts with the Exothermic heat pack surrounding the reservoir. This initiates the heat pack to begin heating. After the oxygen runs out from the first reaction, the heat pack continues to heat by using atmospheric oxygen which comes in through the vents (3) on the outside of the apparatus The exothermic reaction can alternatively only contain two reactions. One is preferably a fast initial reaction that is used to quickly heat the reservoir containing defogging solution or saline. The second reaction is a slower sustained reaction that maintains the temperature within the apparatus above body temperature for a longer period of time.

The initial fast heating of the reservoir is preferably attained by the highly exothermic decomposition of H2O2. Alternatively the fast reaction can be generated from other chemicals such as Sodium acetate and water, Calcium chloride and water. Alternatively a battery and a heating filament can be used to heat the reservoir during the initial fast heating part of the dual reaction.

The second, slower, longer lasting reaction is preferably the oxidation of an iron mixture that contains Iron, vercumulite, water and activated charcoal. The sustained longer reaction can also be a combination of two chemicals located around the sheath. The chemicals can be H2O2, Calcium chloride and water or Sodium acetate and water. It can also be two chemicals that when combined form an exothermic reduction oxidation reaction. Alternatively, energy from a battery may also be used to heat the interior of the apparatus and maintain the temperature of the reservoir above body temperature for a sustained period of time.

A multiplicity of exothermic reactions may occur with a multiplicity of different reactants commonly known to persons skilled in the art.

While the above invention has been described with reference to certain preferred embodiments, the scope of the present invention is not limited to these embodiments. One skilled in the art may find variations of these preferred embodiments which, nevertheless, fall within the spirit of the present invention, whose scope is defined by the claims set forth below.

What is claimed is:

1. A sterilized endoscopic scope defogger comprising:
   a casing made of an insulated substantially rigid material, the casing having sidewalls defining a plurality of sidewall chambers and a central chamber, an outer surface of the casing defining an inlet of a cavity communicating with the central chamber to allow a surgical scope to be inserted into the central chamber through the inlet of the cavity;
   exothermic reactive chemicals including a catalyst disposed within the sidewall chambers;
   a defogging solution disposed within the central chamber and to be heated by the exothermic reactive chemicals, and wherein the sidewall chambers configured to be breachable to create a sustained exothermic reaction in order to heat a surgical scope submerged in and heated via the heated defogging solution; and
   the cavity being self-sealing and configured to allow a surgical scope to be inserted through the inlet of the cavity and to be submerged in and heated via the defogging solution, and to prevent the defogging solution from spilling out of the inlet of the cavity.

2. An endoscopic scope defogger as in claim 1 wherein the cavity is configured for receiving a distal end of an endoscopic lens in order to submerge the distal end in the defogging solution.

3. An endoscopic scope defogger as in claim 1 wherein the catalyst for the heating reaction is in gel form in order to achieve a time delay reaction.

4. An endoscopic scope defogger as in claim 1 wherein said casing includes a shock absorbent material.

5. An endoscopic scope defogger as in claim 1 wherein said casing has an adhesive coupled thereto.

6. An endoscopic scope defogger as in claim 5 wherein said adhesive is hook and loop fasteners.

7. An endoscopic scope defogger as in claim 1 further comprising a wiping cloth coupled to an outer surface of the casing.

8. An endoscopic scope defogger as in claim 7 wherein said wiping cloth is impregnated with a defogging solution.

9. An endoscopic scope defogger as in claim 1 wherein said casing is made of a disposable material.

10. An endoscopic scope defogger as in claim 1 wherein said casing has a compact configuration.

11. A compact portable sterile scope defogger comprising:
    a casing made of an insulated substantially rigid material, an interior of the casing defining a plurality of divided compartments including breachable periphery compartments and a central compartment, an outer surface of the casing defining an inlet of a cavity communicating with the central compartment;
    a predefined number of chemicals disposed in the periphery compartments to achieve a plurality of exothermic reactions upon breaching of the periphery compartments; and
    a defogging solution disposed within the central compartment and to be heated by the chemicals, and wherein the cavity is configured to be self-sealing and the central compartment being shaped to allow a surgical scope to be inserted through the inlet of the cavity into the central compartment and submerged in and heated via the heated defogging solution, and to prevent the defogging solution from spilling out of the central compartment and out of the inlet of the cavity.

12. A disposable compact portable sterile scope defogger comprising:
    a casing made of an insulated substantially rigid material, the casing defining a plurality of periphery compartments and a central compartment, an outer surface of the casing defining an inlet of a cavity communicating with the central compartment to allow a surgical scope to be inserted into the central compartment through the inlet of the cavity;
    chemicals disposed in a portion of the periphery compartments;
    reactive metals disposed in another portion of the periphery compartments adjacent to outer sidewalls of the central compartment;
    ducts interconnecting the periphery compartments;
    breachable membranes separating the periphery compartments, the breachable membranes being configured to be breachable for intermingling of the chemicals to generate an exothermic reaction and for gases generated by the exothermic reaction to travel through the ducts such that the reactive metals react with the gas to further generate a sustained exothermic reaction and to transfer heat to the central compartment; and
    a defogging solution disposed in the central compartment and to be heated by the chemicals, and wherein the cavity is configured to be self-sealing and the central compartment being shaped to allow a surgical scope to be inserted through the inlet of the cavity into the central compartment and submerged in and heated via the defogging solution, and to prevent the heated defogging solution from spilling out of the central compartment and out of the inlet of the cavity.

13. A disposable compact portable sterile scope defogger comprising:
    a casing made of an insulated substantially rigid material, the casing defining a plurality of periphery compartments and a central compartment, an outer surface of the casing defining an inlet of a cavity communicating with the central compartment to allow a surgical scope to be inserted into the central compartment through the inlet of the cavity;
    chemicals disposed in a portion of the periphery compartments;
    reactive metals disposed in another portion of the periphery compartments adjacent to outer sidewalls of the central compartment;
    ducts interconnecting the periphery compartments;
    breachable membranes separating the periphery compartments, the breachable membranes being configured to be breachable for intermingling of the chemicals to generate an exothermic reaction and for gases generated by the exothermic reach on to travel through the ducts such that the reactive metals react with the gas to further generate a sustained exothermic reaction and to transfer heat to the central compartment, and the membranes each retaining a different decomposition characteristic; and
    a defogging solution disposed in the central compartment and to be heated by the chemicals, and wherein the cavity is configured to be self-sealing and the central compartment being shaped to allow a surgical scope to be inserted through the inlet of the cavity into the central compartment and submerged in and heated via the defogging solution, and to prevent the heated defogging solution from spilling out of the central compartment and out of the inlet of the cavity.

14. A compact portable sterile scope defogger comprising:
a casing made of an insulated substantially rigid material, the casing defining a central compartment and a plurality of divided periphery compartments including breachable periphery membranes each having a different decomposition characteristic, the central compartment being defined by sidewalls of the periphery compartments, an outer surface of the casing defining an inlet of a cavity communicating with the central compartment to allow a surgical scope to be inserted into the central compartment through the inlet of the cavity;
a predefined number of chemicals disposed within the periphery compartments to achieve a plurality of exothermic reactions upon breaching of the periphery membranes; and
a defogging solution disposed within the central compartment and to be heated by the chemicals, and wherein the cavity is configured to be self-sealing and the central compartment being shaped to allow a surgical scope to be inserted through the inlet of the cavity into the central compartment and be submerged in and heated via the defogging solution, and to prevent the heated defogging solution from spilling out of the central compartment and out of the inlet of the cavity.

15. A disposable compact portable sterile scope defogger comprising:
a casing made of an insulated substantially rigid material the casing defining a central compartment and a plurality of periphery compartments, an outer surface of the casing defining an inlet of a cavity communicating with the central compartment to allow a surgical scope to be inserted into the central compartment through the inlet of the cavity;
chemicals disposed in a portion of the periphery compartments;
a chemical reaction catalyst disposed within another portion of the periphery compartments, the catalyst being in the form of a gel to achieve a time delayed reaction;
reactive metals disposed in a further portion of the periphery compartments adjacent to outer sidewalls of the central compartment;
ducts interconnecting the periphery compartments;
breachable membranes separating the periphery compartments, the breachable membranes each having a different decomposition characteristic, the breachable membranes being configured to be breachable for intermingling of the chemicals to generate an exothermic reaction and for gases generated by the exothermic reaction to travel through the ducts such that the reactive metals react with the gas to further generate a sustained exothermic reaction and to transfer heat to the central compartment; and
a defogging solution disposed in the central compartment and to be heated by the chemicals, and wherein the cavity is configured to be self-sealing and the central compartment being shaped to allow a surgical scope to be inserted through the inlet of the cavity into the central compartment and submerged in and heated via the defogging solution, and to prevent the heated defogging solution from spilling out of the central compartment and out of the inlet of the cavity.

16. A compact portable sterile scope defogger comprising:
a casing made of an insulated substantially rigid material, the casing defining a plurality of periphery compartments and a central compartment formed by sidewalls of the periphery compartments, an outer surface of the casing defining an inlet of a cavity communicating with the central compartment to allow a surgical scope to be inserted into the central compartment through the inlet of the cavity, the periphery compartments each including a breachable membrane having a different decomposition characteristic;
a predefined number of chemicals disposed in the periphery compartments to achieve a multiplicity of exothermic reactions upon breaching of the breachable membranes; and
a defogging solution disposed in the central compartment and to be heated by the chemicals, and wherein the cavity is configured to be self-sealing and the central compartment being shaped to allow a surgical scope to be inserted through the inlet of the cavity into the central compartment and submerged in and heated via the defogging solution, and to prevent the heated defogging solution from spilling out of the central compartment and out of the inlet of the cavity.

17. A method to defog a surgical scope comprising:
providing a thermally insulated container having a housing defining an inlet for receiving a scope, a defogging solution disposed within the inlet, the inlet being self-sealing to prevent the defogging solution from spilling out of the inlet and breachable chambers containing reactants for heating the defogging solution;
breaching the compartments containing the reactants to produce a sustained exothermic reaction to heat the defogging solution; and
periodically inserting a scope as needed during a surgical procedure within the inlet and submerging the scope in the heated defogging solution to heat the scope via the defogging solution.

* * * * *

UNITED STATES PATENT AND TRADEMARK OFFICE
CERTIFICATE OF CORRECTION

PATENT NO. : 7,311,660 B2 Page 1 of 1
APPLICATION NO. : 10/826866
DATED : December 25, 2007
INVENTOR(S) : Ricardo Alexander Gomez It is certified that error appears in the above-identified patent and that said Letters Patent is hereby corrected as shown below:

Column 12, claim 13, line 59 please delete the words "reach on" and replace with the word --reaction--.

Signed and Sealed this

Twentieth Day of May, 2008

JON W. DUDAS
*Director of the United States Patent and Trademark Office*